United States Patent [19]

Bolta et al.

[11] Patent Number: 5,733,032
[45] Date of Patent: Mar. 31, 1998

[54] MOBILE LIGHT PANEL STAND

[75] Inventors: Charles J. Bolta, 625 Mathews, Fort Collins, Colo. 80524; Francis M. Wile, Fort Collins, Colo.

[73] Assignee: Charles J. Bolta, Fort Collins, Colo.

[21] Appl. No.: 706,304

[22] Filed: Aug. 30, 1996

Related U.S. Application Data

[60] Provisional application No. 60/003,064 Aug. 31, 1995.
[51] Int. Cl.⁶ ........................................................ G09F 13/04
[52] U.S. Cl. .............................. 362/97; 362/1; 362/413; 362/418; 362/287; 362/427; 108/23
[58] Field of Search ........................... 362/33, 97, 1, 362/413, 418, 427, 419, 285, 287; 108/23; 248/454, 474

[56] References Cited

U.S. PATENT DOCUMENTS

| | | | |
|---|---|---|---|
| 2,215,462 | 9/1940 | Davidson, Jr. et al. | 108/23 |
| 2,331,673 | 10/1943 | Fay | 108/23 |
| 3,166,028 | 1/1965 | Zagel | 108/23 |
| 4,303,606 | 12/1981 | Rotter | 362/1 |
| 4,631,643 | 12/1986 | Koster | 362/97 |
| 5,060,118 | 10/1991 | Penrod et al. | 362/250 |
| 5,308,035 | 5/1994 | Ross | 248/454 |

*Primary Examiner*—Thomas M. Sember
*Attorney, Agent, or Firm*—Rick Martin

[57] ABSTRACT

A mobile light panel stand supports a light panel suited to treat humans who are in need of exposure to light in a manner known as light therapy. The stand has two pair of hinged legs. Each pair of legs has a brace member to provide a solid two-legged assembly. The two two-legged assemblies are connected by collapsible braces which allow the device to fold into a narrow posture for passage through doorways. The base of the opened assembly has an anti-tipping wide stance for use by hospitals where patients may lean on the device for support. One set of legs has an upper extension which supports the light panel between the two two-legged assemblies via adjustable nuts and bolts. The light panel can be tilted by adjusting the adjustable nuts.

5 Claims, 3 Drawing Sheets

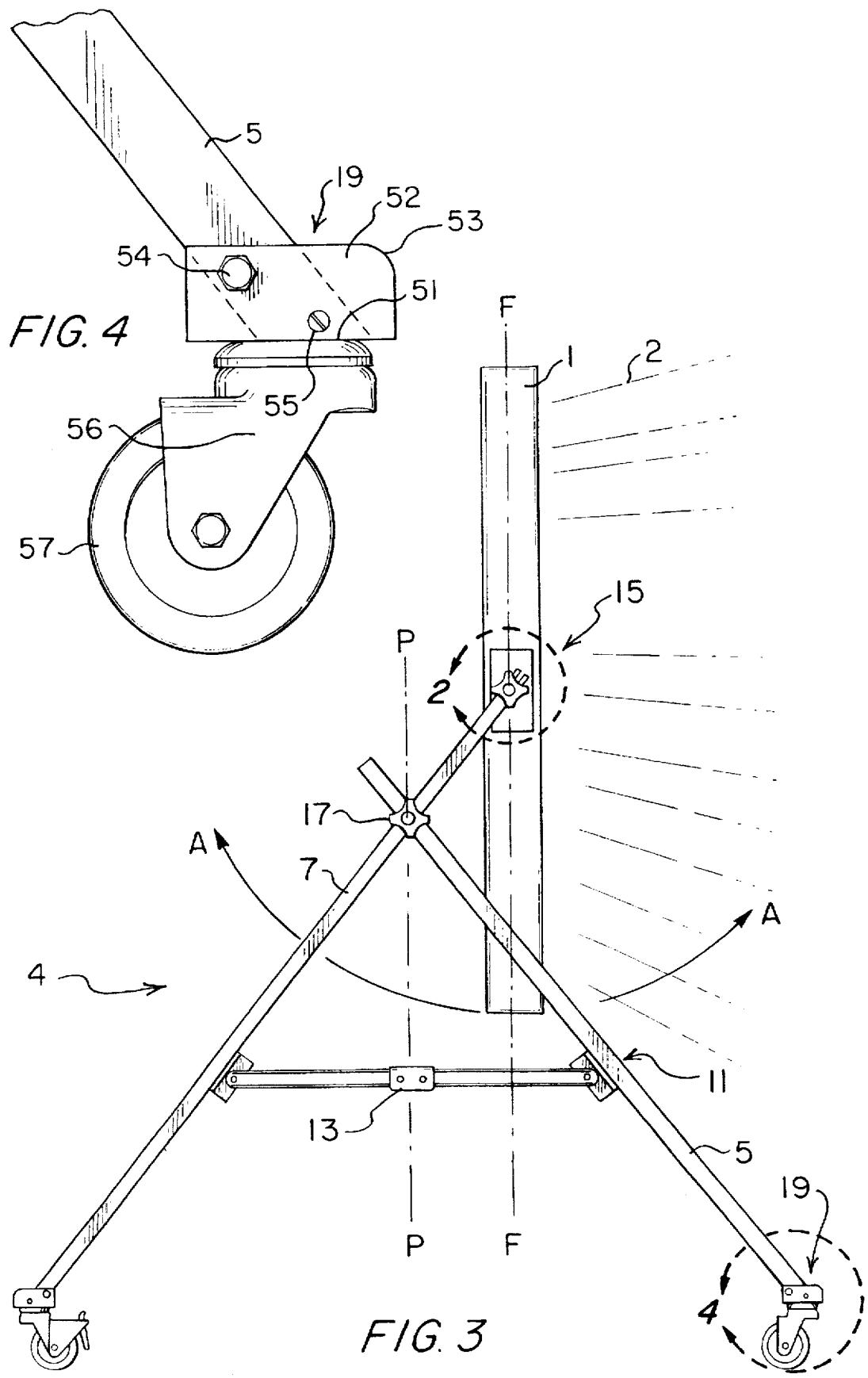

5,733,032

1
MOBILE LIGHT PANEL STAND

This application is based upon and claims priority to United States Provisional patent application Ser. No. 60/003,064 filed Aug. 31, 1995.

FIELD OF INVENTION

This invention generally relates to the field of treatment for a specific medical disorder. Specifically, the system relates to the efficient placement and effective utilization of a particular treatment modality in an institutional or home setting. Through the invention, the disorder, known as Seasonal Pattern or Seasonal Affect Disorder, may be treated efficiently and effectively by subjecting the patient to an electroluminescent lighting source. This source may be a full-spectrum and/or high-lumen output light positioned within an institutional frame. The system also can act to simultaneously shield the patient from certain undesirable electromagnetic fields (EMFs).

BACKGROUND OF THE INVENTION

Little information appears presently available with respect to treating Seasonal Pattern or Seasonal Affect Disorder. Basically, the disorder appears treatable to some extent by subjecting the patient to a full-spectrum light; that is a light which emits throughout the visible spectrum at wavelengths approaching the spectrum at which the sun's light reaches the surface of the earth; that is the wavelengths to which man has been subjected throughout evolution. While this appears simple enough, in actual practice, problems of both a mechanical and electromagnetic nature have not as yet been appropriately addressed.

Problems of a mechanical nature encountered in providing such a system included the type of frame and support structure needed to withstand institutional (i.e., hospitals, nursing homes, etc.) use. It was determined that: a) the frame needed to be foldable for storage; b) the light box removable; c) the entire unit be easily moved from room to room; d) there be no sharp edges, and counter-sunk bolts be used for safety; e) it not be able to be pulled or tipped over; f) the unit be able to be assembled and moved by one person; g) and the unit be strong enough that it would not collapse while in use.

In further considering the nature and effectiveness of the treatment, the question arose as to how to properly shield the EMFs emanating from the lights. It was determined that as there is potentially compelling scientific evidence that suggests that exposure to EMFs may not only generally cause physical and emotional disorders in human beings, but that these impacts might negatively impact the specific treatment being implemented in this case. Thus, it is preferred that the system act to reduce these fields as much as possible.

As to the framing and support elements, other frames were reviewed yet found unusable due to their large size and weight. They were unsuitable for use in many institutional settings i.e., hospitals or other kinds of treatment clinics where space is at a premium. Generally, the requirements for institutional settings are such that any device used for treatment of Seasonal Pattern must be sturdy, strong, movable, and foldable. There is, therefore, a need for a structure that is easily cleansed, requires low maintenance, and is able to hold a large light box specifically designed for institutional use.

Other factors taken into consideration in designing this apparatus were that it would be preferable for it to be easily repaired and cleaned. Also, it should not fall over when in use.

2

To solve the mechanical problems at hand, it was determined that a light was needed which could be quickly and efficiently positioned, allow simple operation, and abundantly illuminate the area where such persons as are using it are seated.

One aspect of the invention is that it can, to some degree, be characterized as presenting techniques and devices others might have had the opportunity to try. This may actually highlight the non-obvious nature of the invention. Although the implementing arts and elements had long been available, those involved in this field simply did not appreciate that the use of these elements was something they could use as effectively as shown here. This can also be surprising because there has been a long felt but unsatisfied need for the invention. Those involved in the Seasonal Pattern area have appreciated that the problem of effective treatment existed. However, the true nature of the problem was not fully seen by those skilled in the art prior to this invention. To some degree, this may have been due to the fact that those skilled in the art failed to understand the problem of properly subjecting the patient to conditions and to providing an easily usable device for treatment. The efforts undertaken may even have acted to teach away from the technical direction taken by this invention. Certainly some of the literature has even acted to not only direct persons away from the direction taken in this invention but also to even create a level of disbelief and incredulity on the part of those skilled in the art that the Patentee's approach is appropriate.

SUMMARY OF THE INVENTION

The main object of the present invention fulfills the requirements outlined. The system may include a foldable, lightweight, aluminum and stainless steel lighting fixture employed for use with full-spectrum lights. It may also incorporate the aspect of the lights being shielded from EMFs. The frame and support preferred is lightweight, portable, and foldable for easy use and storage. The top of the support is also notched making it possible for one person to safely assemble it by sliding the light source or frame into notches.

This invention can also include a foldable stand mounted on wheels and wheel foot supports to allow for mobility, front and rear supports, and a light box with shielding for EMFs. The frame can be made of aluminum and stainless steel, and the unit can be designed to be cleaned with minimum effort. All the parts involved in making the unit may be selected to be obtained from existing manufacturers. The unique structure of the frame ensures that a large light box can be placed upon it and used.

For safety, locking braces can be used for the folding support arms. The arms can be designed to insure that the unit will not tip over when in use as they may provide a broad base of support for the unit as a whole. Large, perhaps even four-inch, tightening-down handles can be employed on either side of the unit so that when the unit is placed within the notches, there is no possibility of it somehow slipping out.

In order to provide a wide base of support, front and rear horizontal supports have been developed. The notch mounting system gives a solid place upon which the light box may be placed and allows for one-person assembly. The lockable, folding arm supports enable the entire invention to be folded up easily by one person. They also provide added support to the unit as a whole. The wheels are particularly durable, and the wheel support foot gives an added safety feature to the unit. Upon consideration of all factors, it may be desirable that in order to provide the best mode of light possible, the light box may preferably contain either full-spectrum, high lumen, lux, or foot-candle bulbs. This may be preferable because the person utilizing this invention may have specific preferences as to the type of light they will receive from it. The inclusion of a parabolic lens makes it possible for the EMFs to be reduced from the front of the unit. It has been found that treatment in this way provides the best mode of alleviating the condition. The person receiving the light is not also being subjected to EMF emissions.

The light box is supported in such a way that allows the light box to be angled as needed. This way, the person using the light has the maximum amount of light possible. The forward positioning of the light box also allows the light to be moved as close as possible to the person using it. The front horizontal support bar allows the light box to swing freely and also adds substantial support strength. The design is strong. For instance, the inventors were able to stand on the support frame without any signs of collapse or damage. The front horizontal bar can be adjusted upon manufacturing to compensate for a larger or smaller light box. The front and rear horizontal support bars are placed as close as possible to the light box to give minimum width. This allows the invention to fit through doorways.

The folding arm mounting brackets allow the invention to fold up (via the folding arm supports), and, also, they prevent the invention from falling over while in process of being folded up. The brackets stop it from falling over in that the brackets were built and positioned to stop the invention from folding any further than a point that would bring it off balance. If further folding is needed for storage, one can remove the light box, which allows for one side of the folding support arms to be unbolted. The support frame can then lie flat or stand completely upright. A safety strap or bar can be used when the support frame is in an upright folded position to stop the frame from unfolding.

The pivot point has a low-friction washer between the vertical frame tubes. This allows the invention to fold easily. It can be located at different points depending upon the size of the light box being used. The handle can be tightened or loosened to hold the vertical tube supports in one of many possible positions. In this way, the invention can be moved or wheeled into tight spaces yet still be safely upright and usable. In addition, the function of wheeling the unit may be exchanged for utilizing skids when there is no need for the unit to be wheeled from place to place.

The front horizontal support bar was placed on the front folding arm bracket to further flush-mount the bar. This minimizes the amount of potential injury to persons using the invention. The notched mounting system was developed so that one person could mount and securely attach the light box to the support frame. The spindle on the light box mounting system slides safely into the notched mounting system. The light box mounting plate and spindle is mounted to the light box with bolts that are flush-mounted to the plate. This allows the box to swivel frontwards and backwards. The nuts are placed in light box allowing for easy assembly, depending upon the size of the light box. The mounting plate can be adjusted as well, depending upon the size of the light box. There is a low-friction washer that allows the light box to be easily adjusted to varying angles by tightening or loosening the black handle. The insert is placed inside the tip of the notched mounting system after the spindle and handle are in place but before the handle is tightened, or the insert could have a hole drilled through it and placed on the spindle before the light box is mounted and then put into notched system. This insert, thereby, keeps the vertical support tubes from squeezing together and failing due to stress upon them.

The invention can be wheeled or slid by the use of the wheel support foot. A wheel is bolted to the wheel support foot. A plate can also be bolted to the wheel support foot which would allow for a larger surface area i.e., as needed for a wood floor or rug. Low- or high-friction material can be attached to the base of this plate to address the sliding of the device on various floors.

The wheel support foot attaches to the vertical support frame tube. Note that the vertical frame tube is cut on an angle. This angle can vary depending upon the length of the folding arms. This keeps the wheels and wheel support feet parallel to the floor. A set screw allows the use of one bolt in firmly securing the wheel support foot to the vertical support frame tube. The corners of the wheel support foot are rounded in the front so that there are no sharp or rough edges. The wheel support foot can also be cut back to flush-mount to the vertical support tube. The wheels can also be made to be either locking or non-locking, swivel base or stationary.

An optional parabolic lens is grounded to the metal frame of the light box with a wire. This grounding lowers the amount of measurable EMFs being emitted by the light box when turned on (as measured by the amount of 60 Hz AC voltage detectable near the surface of the lens at distances of up to one meter). This can be important because it appears that certain emissions can actually match, or at least impact, low-frequency brainwave and other biological patterns. In spite of the fact that the light can often operate at a household frequency (60 Hz), it appears that varying frequency EMFs are possible. The grounding feature on the lens structure can act as an RF filter or to otherwise serve to mitigate the effect of EMFs. It also can act to avoid allowing an impact on the patient regardless of the exact nature of the effect. The parabolic lens can also be used to maximize the amount of full-spectrum light able to come through. It has also been found that with a larger 18 cell parabolic lens in a 4'×2' fixture, the measurable EMFs are not removed to a level the inventors found satisfactory. The use of a one-inch mesh wire attached perpendicularly to the parabolic lens lowered the measurable EMFs to a satisfactory level and also allowed for a maximum amount of full-spectrum light to come through the lens.

An electronic ballast and radio frequency filter were found to have a lower electromagnetic field than magnetic ballast. Further shielding was added to reduce electromagnetic fields as much as possible. The shielding added is comprised of 0.020 nickel alloy mu metal.

Each unit comes complete with an on/off switch and a standard three-prong plug. The light box can be preassembled, or each part of the stainless steel and aluminum frame can be marked for quick assembly. Once turned on, the unit automatically produces the predetermined amount of high lumen or full-spectrum light, and the EMF emissions are reduced through proper design as discussed earlier.

In general terms, the support frame can serve as a means for the light box to be safely portable. The light box can serve as a means for performing the function of providing the closest to natural sunlight possible aiding in the treatment of Seasonal Pattern.

As mentioned, the support frame can be used with many different types of light fixtures (fluorescent, halogen, incandescent, or high-intensity discharge lamp fixtures) for a variety of purposes. For the treatment of Seasonal Pattern, however, the full-spectrum light appears most effective.

The end result goals of this invention include that a person may use this invention to treat Seasonal Pattern as it provides the closest to natural sunlight possible while possibly simultaneously mitigating the potentially harmful effects of EMF emissions. This mitigation of EMFs takes into consideration that it is believed that a person with Seasonal Pattern may already be in a deteriorated physical and/or emotional state, and therefore more susceptible to EMFs. It is also preferred that it be able to be assembled and used by one person. Another goal is that the unit be durable enough to withstand years of institutional use.

Aluminum and stainless steel components can be used to make the unit lightweight; yet it is also possible for the framing system to be made out of other materials (including but not limited to plastic, wood, and the like). Similarly, although the description may be couched in terms of a specific kind of element (i.e., a tubular element, etc.), it should be understood to encompass all varieties of other elements as well (i.e., solid plates and other support structures). The unit is able to be washed, and all parts of the unit are able to be replaced. Being made of aluminum and stainless steel, the unit is extremely durable. The folding arm supports provide a wide base of support for the unit, making it difficult to damage the unit by putting stress upon the framing system.

The notched mounting system can make it possible for one person to assemble the unit. Having the foldable arm supports and wheels makes it functional for one person to use and move as needed. It is also uniquely suited for institutional use in that it is able to be stored with a minimum of space needed when not in use. It if is preferred that the unit take up even less space when in use and when folded up, it is possible to shorten the folding arm supports or even make them telescopic, thereby making the entire unit shorter when extended and when stored in its upright folded position.

In accomplishing the treatment desired, a number of steps are possible. The patient can be subjected to varying times or levels of exposure. This can be built up over the course of days or weeks or can be a limited number of gentle or intense treatments. It may be timed to coincide or be cyclincal with the patient's circadian, daily, or other biological rhythms. They may also be varied based upon meteorological conditions. The system can be implemented by analyzing the patient. This can include measuring specific characteristics of the patient. Then the treatment can include determining an appropriate treatment regimen, and then establishing the devices so as to implement that regimen. This establishment can be accomplished automatically through proper device design. This can also involve automatic or manual timing to both initiate and terminate treatment. The device may also act manually or automatically to avoid sharp changes in conditions. There can also be changes in the intensity of illumination along the surface of the light or at the patient's location if desired. Automatic positioning features can be included where it is deemed necessary either for safety or for treatment.

As mentioned, it is possible that this invention as described may be used in alternative settings i.e., as an industrial light frame for other applications, or as an artist's light. As stated in the previous paragraphs, a broad disclosure is to be understood from the foregoing discussion. Certainly, elements of the invention as described in this application may be modified or changed without changing the essential nature of the invention. The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

Equivalent, broader, and more generic terms are implicit in the prior description of each element. Such terms can be substituted where desired to make explicit the implicitly broad coverage to which this invention is entitled. Further, it should be understood that a variety of changes may be made without departing from the essence of the invention. Such changes are also implicitly included in the description. They still fall within the scope of this invention. A broad disclosure encompassing both the explicit embodiments shown, the great variety of implicit alternative embodiments, and the broad methods or processes and the like are encompassed by this disclosure and may be relied upon when drafting the claims for the full patent application. It should be understood that such language changes and broad claiming will be accomplished when the Applicant later (filed by the required deadline) seeks a patent filing based on this provisional filing. The subsequently filed, full patent application will seek examination of as broad a base of claims as deemed within the Applicant's right and will be designed to yield a patent covering numerous aspects of the invention both independently and as an overall system.

In general, it is an object of the present invention to provide a portable, easily assembled and movable frame to hold a light box that contains full-spectrum, high lumen output bulbs, while also providing shielding from measurable electric fields.

Another object of the present invention is to provide full-spectrum light that provides light that is the closest to natural sunlight available. It should also provide very high lumen, lux, or foot-candle output.

Another object of the present invention is that the patient be shielded from the potentially harmful effects of EMF emissions. Included in the goal of shielding is reducing the measurable AC electric field through the front parabolic or other lenses, with minimal loss of light.

Another object of the invention is that it be large enough to hold either a light box that provides sufficient full-spectrum light or a high-intensity fixture to treat Seasonal Pattern.

Another object of the present invention is to provide a particularly novel notching system on the frame that makes it easy for one person to assemble and disassemble the lighting system.

Other objects of this invention will appear from the following description and appended claims, reference being made to the accompanying drawings forming a part of this specification wherein like reference characters designate corresponding parts in the several views.

BRIEF DESCRIPTION OF THE DRAWINGS

FIG. 3 is a side plan view of the preferred embodiment shown in the open position.

FIG. 4 is a side plan view of the caster.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 1:
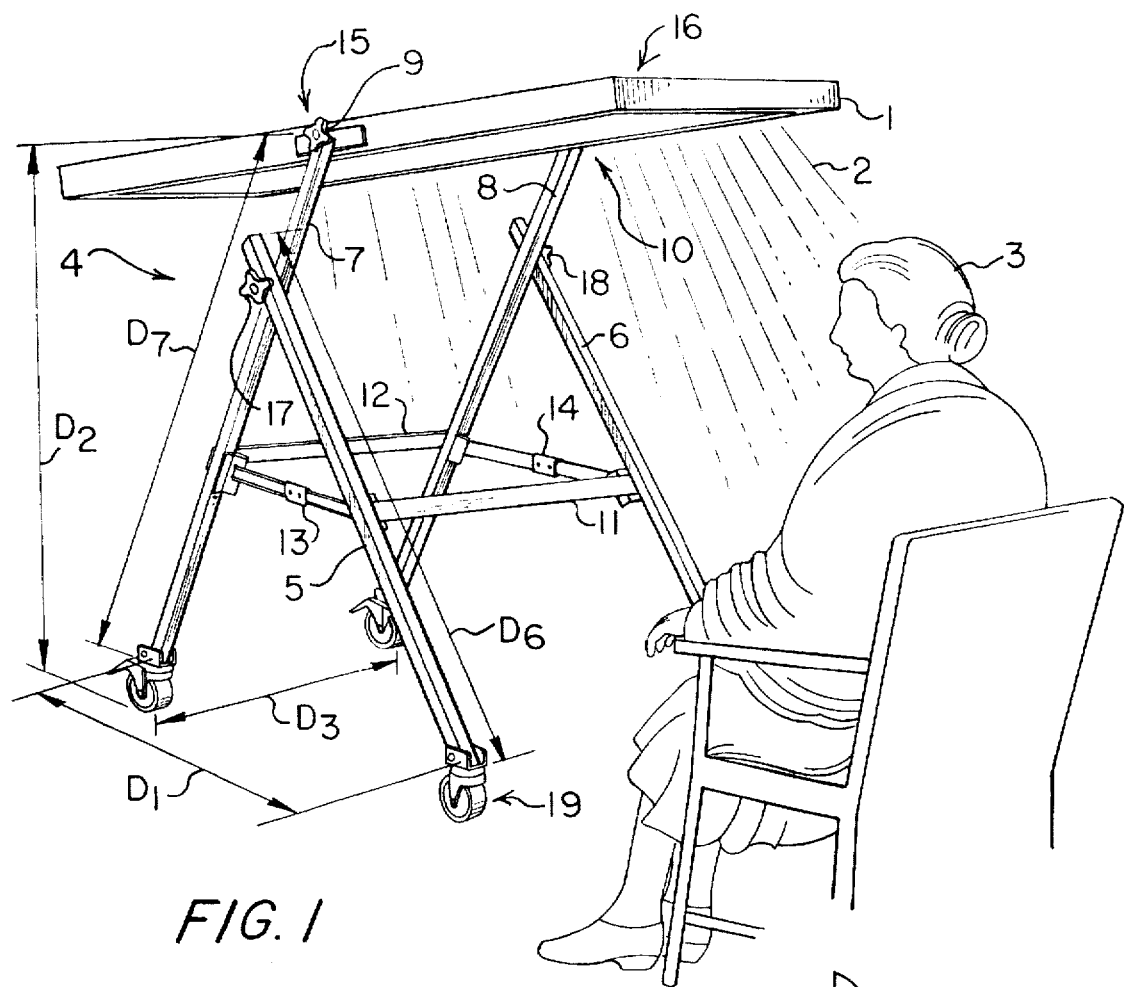
FIG. 1 is a front perspective view of the preferred embodiment.
Figure 5:
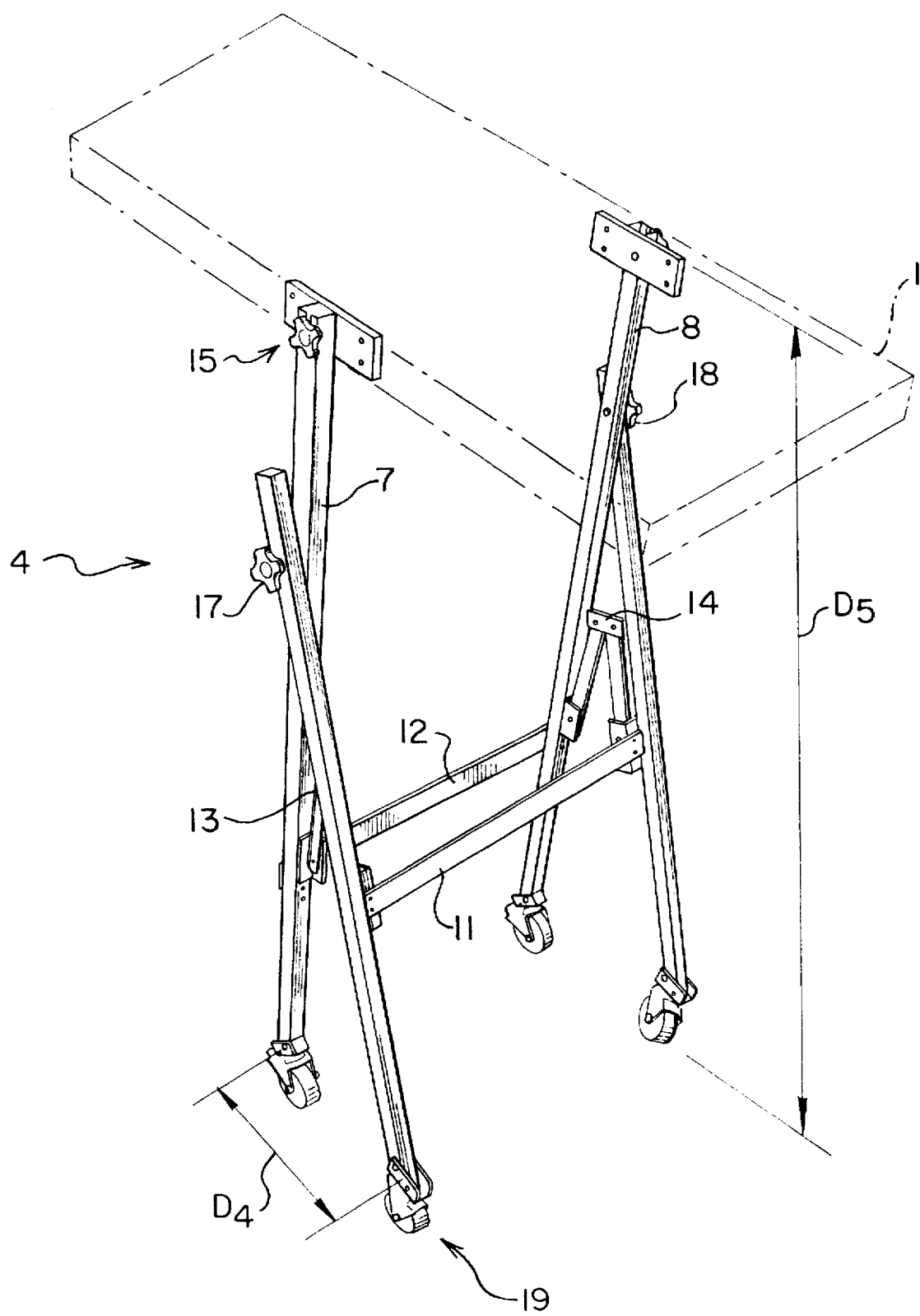
FIG. 5 is a top perspective view of the preferred embodiment in the folded position.

Referring first to FIG. 1 a light panel 1 is emitting light rays 2 to a patient 3. Preferably bringing the light panel within 12-24 inches from the patients. A stand 4 has parallel legs 5, 6 which are held in a rigid H-assembly by front brace 11. The rear parallel legs 7, 8 are likewise held in a rigid H-assembly by rear brace 12. The pair of rigid H-assemblies are pivotally joined by nut and bolt fasteners 17, 18. Folding lock arms 13, 14 allow the stand to fold for passage through doorways as shown in FIG. 5. Caster assemblies 19 provide a mobile stand. Nominal dimensions are d1=54", d2=51½", d3=26½", d4=18⅛", d5=61⅛".

The light stand 1 is easily removed or easily tilted by means of slot assemblies 15. Rear legs 7, 8 are longer than front legs 5, 6. Thus, rear legs 7, 8 extend forward over front legs 5, 6 which enables the light panel 1 to extend forward of bolt fasteners 17, 18 as best seen in FIG. 3. The longer rear legs 7, 8 also allow the light panel 1 to clear the front brace 11 as shown by arrows A—A of FIG. 3. Bolt fasteners 17, 18 are located in the central plane P—P of open stand 4. The light stand 1 is supported forward of the central plane P—P in plane F—F in FIG. 3. The light stand is tiltable in a 360° rotation above the front brace 11 and forward of the central plane P—P. The opened stand 4 forms a double inverted V-frame for a tilt resistant stance on the floor.

Figure 2:
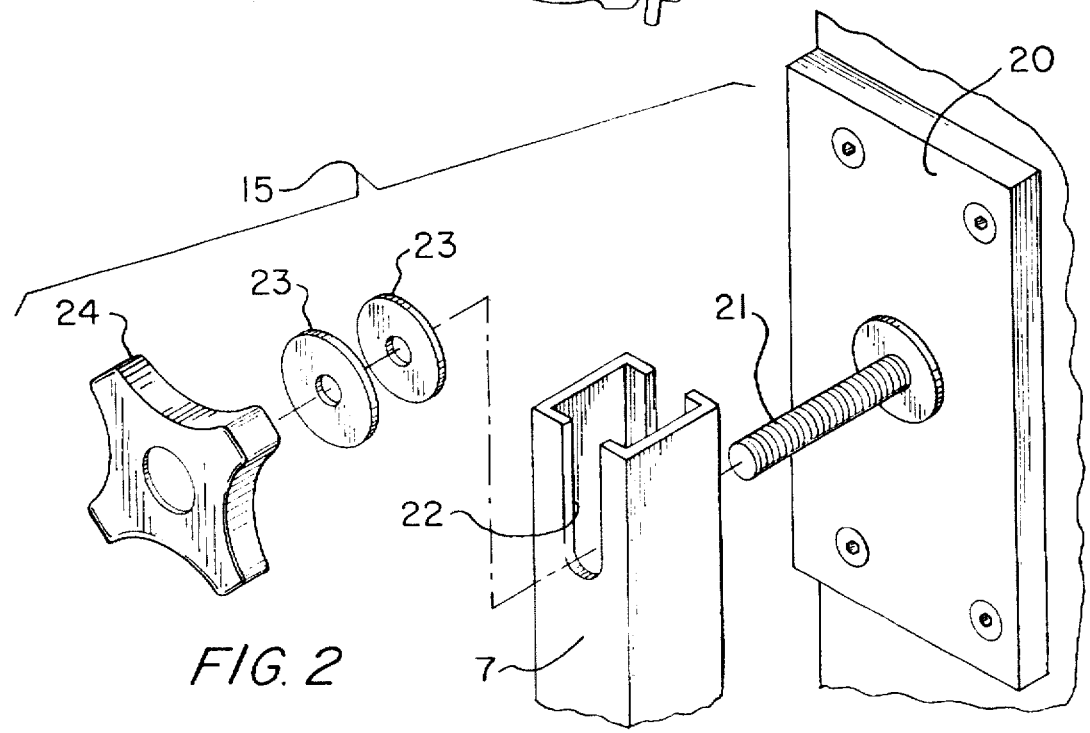
FIG. 2 is an exploded view of the light panel support assembly.

Referring next to FIG. 2 the light panel support assembly 15 comprises a brace 20 mounted on the light panel 1. The brace 20 supports a bolt 21 which mounts in slot 22 on the top of leg 7. Washers 23 allow bolt 24 to be hand fastened to provide a tilt adjustment and a locked position and a removal position.

Referring next to FIG. 4 the leg 5 has a level bottom 51. A caster mounting bracket 52 has a smooth leading edge 53 for safety. Bolt 54 secures the caster mounting bracket 52. Screw 55 secures the caster mounting bracket 52 which supports the wheel 57. The wheel 3 and caster 56 is mounted by a hole in caster mounting bracket 52 and bolted down. (Not shown).

Although the present invention has been described with reference to preferred embodiments, numerous modifications and variations can be made and still the result will come within the scope of the invention. No limitation with respect to the specific embodiments disclosed herein is intended or should be inferred.

We claim:

1. A light panel stand comprising:

a front pair of parallel support legs having a front support bracket forming a front rigid assembly;

a rear pair of parallel support legs having a rear support bracket forming a rear rigid assembly;

a hinge means functioning to join the front and rear rigid assemblies together in a folded and an open position forming a central vertical plane intersecting the front and rear pair of parallel support legs, wherein the open position forms a double-inverted V-frame;

a folding brace means functioning to lock the front and rear rigid assemblies in the open position thereby forming a tilt-resistant frame;

said rear pair of parallel support legs having an extension forward over the front pair of parallel support legs and forward of the central vertical plane;

a pair of open notches located at the extension forward over the front pair of parallel support legs; and a pair of light panel support bolts pivotably and removably supporting a light panel in a 360° rotation between the front and rear rigid assemblies and above the front support bracket.

2. The stand of claim 1, wherein the first and second pair of parallel support legs each have a caster on each member of the pair, thereby providing a mobile stand.

3. The stand of claim 1, wherein the folding brace means further comprises a folding lock arm.

4. The stand of claim 1, wherein the light panel support bolts further comprise a pair of handles having nuts to lock the pair of bolts.

5. The stand of claim 1, wherein the hinge means further comprises a bolt and a nut.

* * * * *